United States Patent [19]

Sugihara et al.

[11] 4,041,079

[45] Aug. 9, 1977

[54] BICYCLIC COMPOUNDS

[75] Inventors: Hirosada Sugihara, Osaka; Michio Motohashi, Kobe; Masazumi Watanabe, Osaka; Masao Nishikawa, Kyoto; Yasushi Sanno, Osaka, all of Japan

[73] Assignee: Takeda Chemical Industries, Ltd., Osaka, Japan

[21] Appl. No.: 424,315

[22] Filed: Dec. 13, 1973

[30] Foreign Application Priority Data

Dec. 18, 1972 Japan .................. 47-126970

[51] Int. Cl.² ............................................ C07C 91/40
[52] U.S. Cl. ................. 260/574; 260/345.5; 260/430; 260/473 R; 260/501.18; 260/521 R; 260/544 D; 260/562 P; 260/566 A; 260/566 AE; 260/566 F; 260/575; 424/283; 424/316; 424/330
[58] Field of Search ........................................ 260/574

[56] References Cited

U.S. PATENT DOCUMENTS 2,549,685  4/1951  Heinzelmann ............... 260/574 X
3,534,055  10/1970  Gittos et al. ................. 260/295
3,930,022  12/1975  Hauck et al. ................. 260/574 X

OTHER PUBLICATIONS

Thrift, "Journal Chemical Society", C, pp. 288–293 (1967).

*Primary Examiner*—Robert V. Hines
*Attorney, Agent, or Firm*—Wenderoth, Lind & Ponack

[57] ABSTRACT

Novel bicyclic compounds of the general formula:

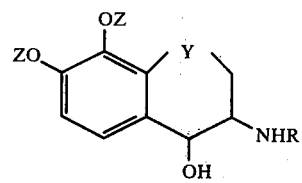

wherein Y stands for —O— or a methylene group, Z stands for hydrogen or an alkyl group having 1 to 6 carbon atoms and R stands for hydrogen or an alkyl group having 1 to 6 carbon atoms are useful as medicines for treatment of asthma or arrhythmia.

8 Claims, No Drawings

BICYCLIC COMPOUNDS

This invention relates to a novel compound of the general formula:

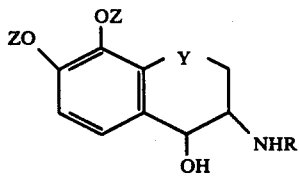

wherein Y stands for —O— or a methylene group, Z stands for hydrogen or an alkyl group having 1 to 6 carbon atoms and R stands for hydrogen or an alkyl group having 1 to 6 carbon atoms, which is useful as medicines for the treatment of asthma or arrhythmia.

As medicines for the treatment of asthma, isoproterenol and metraproterenol, both of which have an action of stimulating beta-adrenergic receptors, have been widely employed. However, while isoproterenol has a bronchodilator action which is said to be associated with $\beta_2$-adrenergic receptors, it has potent cardiac stimulation side effects which are said to be associated with $\beta_1$-adrenergic receptors; metaproterenol on the other hand has only moderate side effects of the above type but is inferior in bronchodilator activity. Therefore, neither of them is satisfactory.

The above situation provided an impetus to our intensive research, which has led us to success in synthesizing novel compond (I), which has more potent bronchodilator activity than isoproterenol and, yet, has only moderate, or is substantially devoid of, $\beta_1$-adrenergic stimulation effects.

Thus, the principal object of the present invention is to provide the compound (I) and its pharmaceutically acceptable salts, which are useful as medicines for treatment of asthma or arrhythmia.

Another object of the present invention is to provide processes for the production of the compound (I) and its salts.

The present compound (I) is produced by reducing a compound of the general formula:

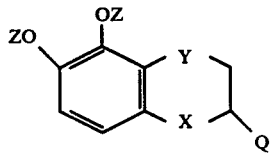

wherein Y and Z have the same meaning as above, X stands for

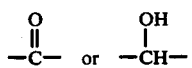

and Q stands for an amino or alkylamino group of the general formula —NHR (wherein R has the same meaning as above), an acylamino group of the general formula —NHCOR₁(wherein R₁ stands for hydrogen or a lower alkyl group having 1 to 5 carbon atoms) or an alkylideneamino group of the general formula

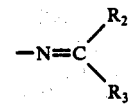

wherein R₂ and R₃ are same or different and each stands for hydrogen or a lower alkyl group having 1 to 5 carbon atoms, the number of carbon atoms included in both lower alkyls R₂ and R₃ being not more than 5), with the proviso that the case where X stands for

and Q stands for an amino or alkylamino group is excluded.

Referring to the above general formula (I) and (II), the alkyl group denoted by Z or R may be straight or branched and is not more than 6 carbon atoms. For this alkyl group, there are enumerated methyl, ethyl, n-propyl, i-propyl, n-butly, i-butyl, sec-butyl, t-butyl, n-pentyl, i-pentyl, 2-methybutyl, 1-methylbutyl, neopentyl, 1,2-dimethylpropyl, t-pentyl, 1-ethylpropyl, n-hexyl, i-hexyl, 3-methylpentyl, 2-methylpentyl, 1-methylpentyl, 3,3-dimethylbutyl, 2,3-dimethylbutyl, 1,3-dimethylbutyl, 2,2-dimethylbutyl, 2-ethylbutyl, 1,2-dimethylbutyl, 1-ethylbutyl, 1,2,2-trimethylpropyl, 1,1,2-trimethylpropyl, and 1-ethyl-2-methylpropyl.

For the lower alkyl groups which is represented by R₁ in case that Q in general formula (II) stands for —NHCOR₁ or which is represented by R₂ or R₃ in case that Q in general formula (II) stands for

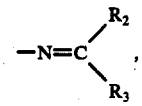

there are enumerated methyl, ethyl, n-propyl, i-propyl, n-butyl, i-butyl, sec-butyl, t-butyl, n-pentyl, i-pentyl, 2-methylbutyl, 1-methylbutyl, neopentyl, 1,2-dimethylpropyl, t-pentyl, and 1-ethylpropyl.

The reduction reactions in the above process are ordinarily conducted by a reducing procedure suitably selected, according to the starting material employed, from conventional ones such as (1) catalytic reduction with platinum, palladium or the like by way of catalyst, (2) reduction by means of a metal hydride such as lithium aluminum hydride, lithium borohydride, lithium cyanoborohydride or the like, (3) Meerwein-Ponndorf-Verley reduction by means of aluminum alkoxide, e.g. aluminum isopropoxide, (4) reduction by means of sodium metal, magnesium metal or the like with, for example, alcohol, (5) reduction by means of zinc dust with e.g. caustic alkali, (6) reduction by means of a metal such as iron or zinc with acid such as hydrochloric acid or acetic acid, (7) electrolytic reduction, and (8) reduction with the aid of reducing enzymes. It should be understood that, aside from the above procedures, any method can be employed that is able to reduce a carbonyl group to an alcohol or to saturate a double bond of an alkylideneamino group. While the reaction temperature varies with different reduction procedures, it is preferably within the range of −20° to 100° C, generally speaking. This reaction is ordinarily carried out at atmospheric pressure but, under certain circumstances, may be conducted at reduced or elevated pressure. The reduction reactions are usually conducted in the presence of a suitable solvent. The solvent is of optional type, insofar as it is capable of dissolving, more or less, the starting material and will not adversely affect the reaction, such as water, an alcohol (e.g. methanol, ethanol, propanol, etc.) an ether (e.g. dimethyl ether, diethyl ether, methyl, ethyl ether, tetrahydrofuran, dioxane, etc.), an ester (e.g. ethyl acetate, butyl acetate, etc.), a ketone (e.g. acetone, methyl ethyl ketone, etc.), an aromatic hydrocarbon (e.g. benzene, toluene, xylene, etc.), organic acid (e.g. acetic acid, propionic acid, etc.) or a mixture of two or more thereof.

In the method of the present invention, starting materials of the general formula (II) include various compounds, giving respectively corresponding object compounds. Thus, in accordance with the starting material and the desired object compound, the suitable reduction means and conditions are selected from those mentioned above.

For example, in a case where a compound (II) wherein X is

Z is an alkyl group and Q is amino or an alkylamino is employed as the starting material i.e.

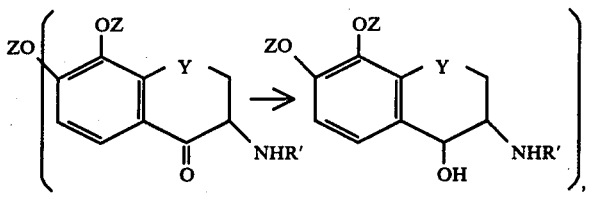

(R' H or an alkyl having 1 to 6 carbon atoms), the reduction means and conditions can optionally be selected from those mentioned before, and in case where a compound (II) wherein X is

Z is hydrogen and Q is amino or an alkylamino is employed as the starting material, the catalytic reduction is preferably used.

In a case where a compound (II) wherein Q is —NHCOR$_1$ is employed as the starting material.

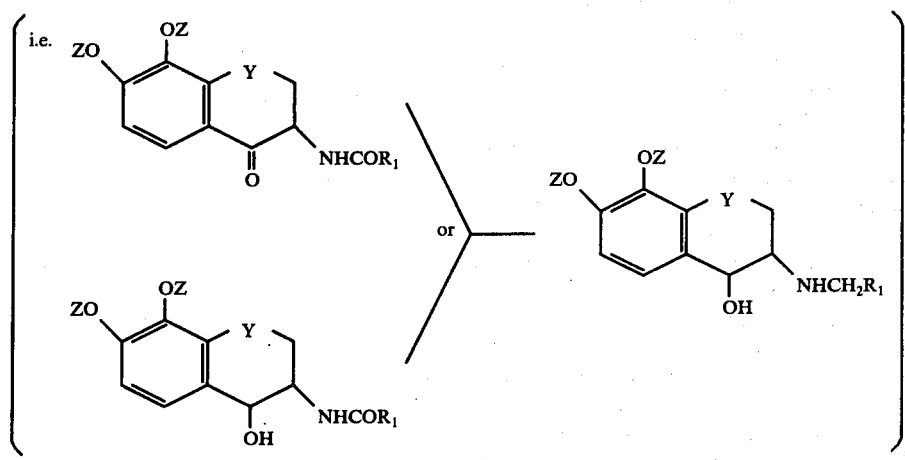

relatively severe reduction conditions are required. The most typical means for this purpose is reduction by using the procedure (2) mentioned above under heating at about 40° to about 100° C.

In the case mentioned just above, when a compond (II) wherein X is $$-\underset{\underset{O}{\|}}{C}-$$

is employed, it is assumed that a compound (II) wherein X is $$-\underset{\underset{OH}{|}}{CH}-$$

is intermediately produced.

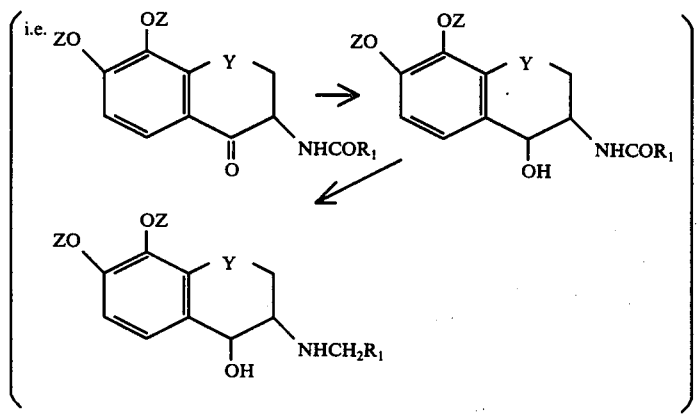

In a case where a compound (II) wherein Q is

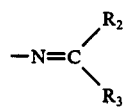

is employed as a starting material

wherein $R_2$ and $R_3$ have the same meaning as above. In this connection, when the compound (II) wherein Q is

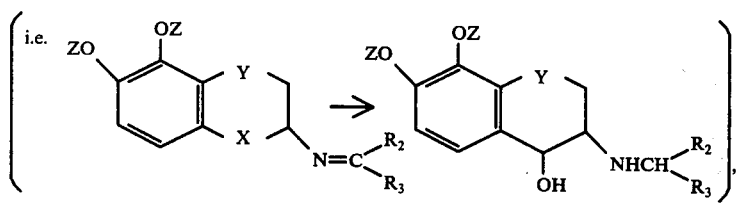

reduction procedures (1) and (2) mentioned above are preferably employed.

This compound (II) wherein Q is

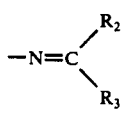

is prepared by reacting the compound (II) wherein Q is an amino group with a ketone or aldehyde of the general formula:

an amino group is subjected to reduction procedure (1) or (2) as mentioned above in the presence of a ketone or aldehyde of the general formula (III), the compound (I) wherein R is the corresponding alkyl group is produced, and in this case it is assumed that the compound (II) wherein Q is an amino group first reacts with the compound (III) to give rise to a compound (II) wherein Q is

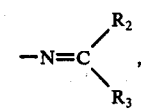

which, in turn, is reduced to give a compound (I) wherein R is the corresponding alkyl group.

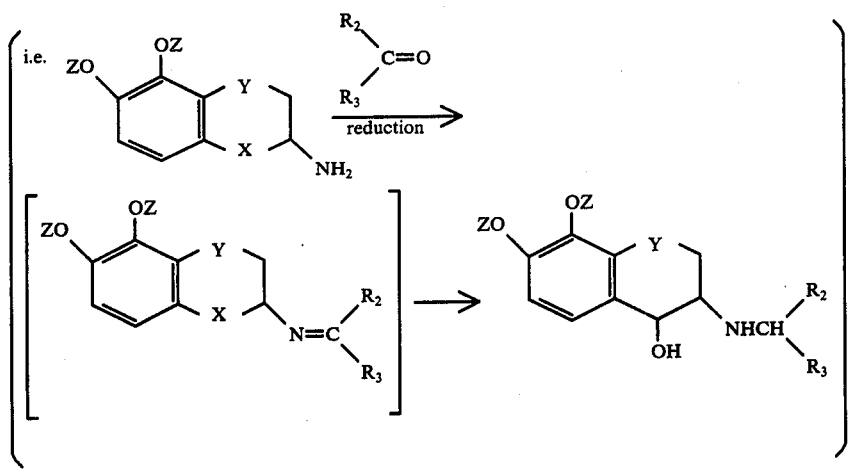

The compounds of general formula (I) thus obtained, include a few asymmetric carbon atoms and, accordingly, occur as some isomers. The racemic mixtures may, if desired, be resolved by conventional manners, for example, by causing the isomers to form salts with optically active acids or bases or by utilizing the principle of physical adsorption on porous resin adsorbents. By way of example, the procedure of reducing 7,8-dihydroxy-3-aminochromanone(4) catalytically in the presence of palladium catalyst under acid conditions, adding acetone to the reduction product, making the mixture weakly basic and further subjecting it to catalytic reduction with platinum as a catalyst causes an isopropyl group to be introduced into the amino group, thereby giving rise to cis-7,8-dihydroxy-3-isopropylaminochromanol-(4).

On the other hand, if the same starting material is reacted throughout under weakly basic conditions, as established by sodium acetate, from the time of reduction with palladium and onwards, trans-7,8-dihydroxy-3-ispropylaminochromanol-(4) is almost stereospecifically obtained.

The compound (I) can be collected as salts with inorganic acids, e.g. hydrochlorides, hydrobromides, sulfates, etc. or as salts with organic acids, e.g. acetates, maleates, tartrates, citrates, etc.

The compounds of general formula (II), in which Y is a methylene group, Z is an alkyl group and Q is an amino group can be produced in the following manner.

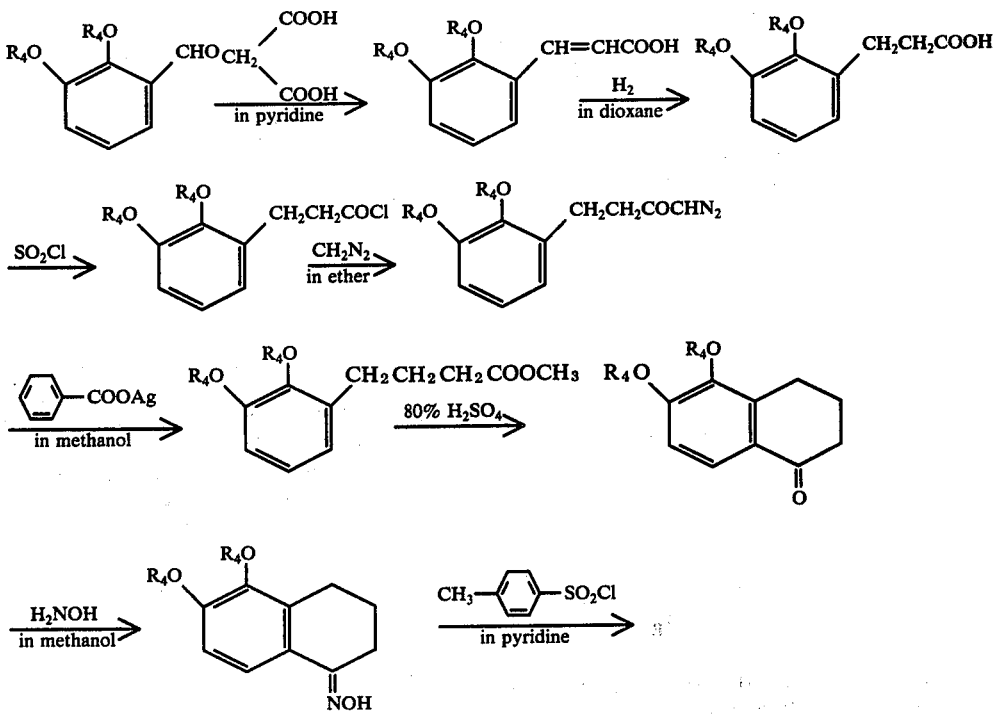

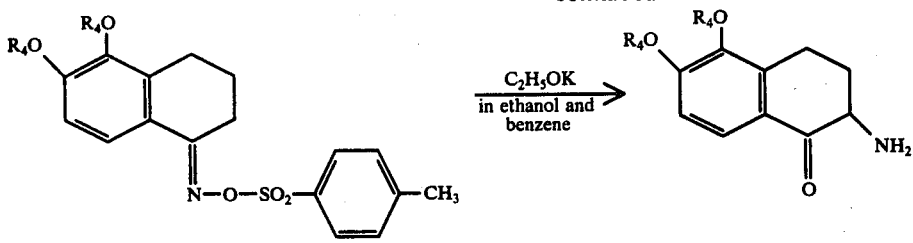

(wherein R₄ stands for an alkyl group having 1 to 6 carbon atoms).

Among the compounds of general formula (II), the compounds in which Y is —O—, Z is an alkyl group and R₁ is a hydrogen atom can be produced in the following manner.

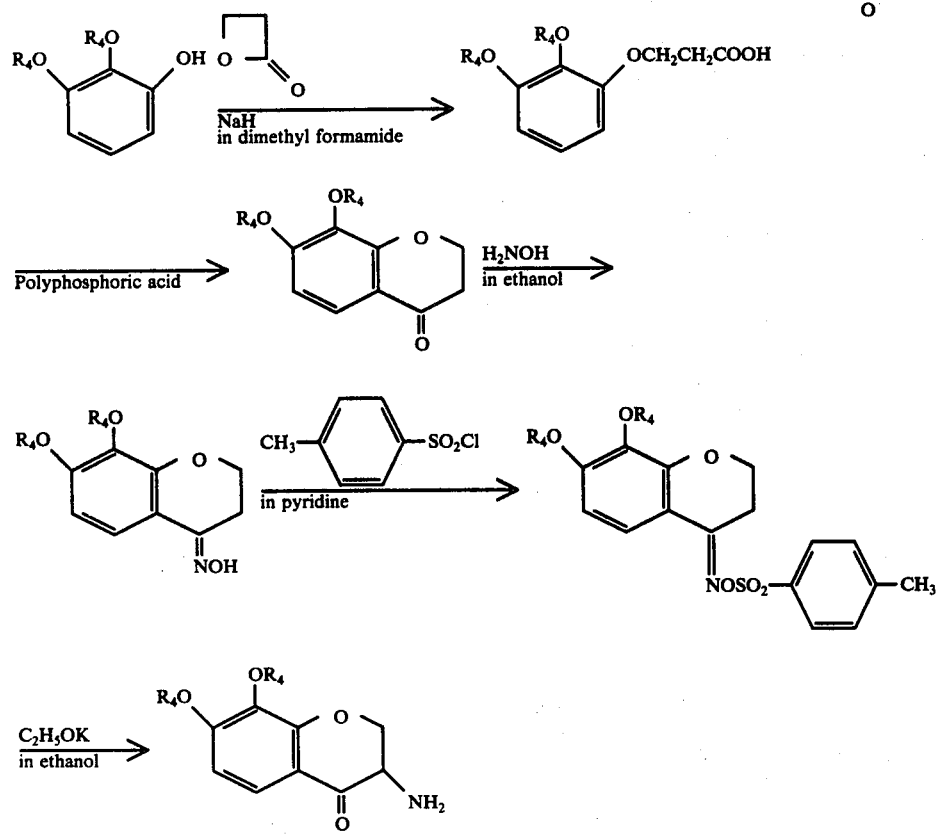

(wherein R₄ has the same meaning as above)

The compounds of general formula (I) can be used for the prophylaxis and treatment of asthma or arrhythmia and can be administered in such dosage forms as oral preparation, injections, sprays and so forth. While the dosage varies somewhat according to the route of administration, it is ordinarily within the range of 0.0004 to 0.4 mg./kg. body weight daily for a human, namely, generally about 0.02 to about 20 mg. a day for human adults.

For further explanation of the present invention, following examples are given wherein the word "part(s)" is based on weight unless otherwise noted, and the relation between "part" and "volume part" corresponds to that between gram and milliliter.

Reference EXAMPLE 1

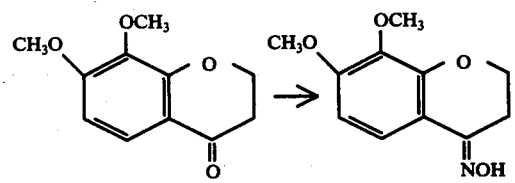

Together with 8 parts of hydroxylamine hydrochloride, 8 parts of anhydrous sodium acetate and 50 volume parts of ethanol, 5.6 parts of 7,8-dimethoxychromanone-(4) is heated on reflux for 6 hours. The reaction mixture is poured in 200 volume parts of ice-water and the resulting precipitate is harvested by filtration, washed with cold methanol and dried. The procedure gives 7,8-dimethoxychromanone-(4) oxime. Melting point: 115° C

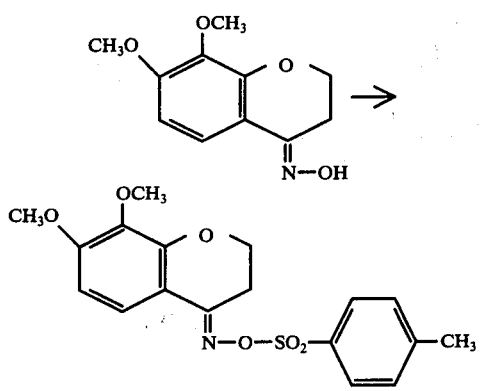

In 60 volume parts of pyridine is dissolved 14.8 parts of 7,8-dimethoxychromanone-(4) oxime and at the bath temperature of 0 to − °C, 14 parts of p-toluenesulfonyl chloride is added. After the addition has been completed, the mixture is stirred at the above temperature for 2 hours and, then, allowed to stand overnight. It is poured in 500 volume parts of ice-water and the resultant precipitate is harvested by filtration, washed with cold methanol and dried. The procedure gives 7,8-dimethoxychromanone-(4)O-(p-toluenesulfonyl)-oxime. Melting point: 128°-129° C.

Elemental analysis, $C_{18}H_{19}NO_6S$: Calcd.: C, 57.28; H, 5.07; N, 3.71. Found: C, 57.08; H, 5.00; N, 3.68.

Infrared absorption spectrum, $\gamma KBr/max$ cm$^{-1}$: 1623, 1598

Nuclear magnetic resonance spectrum, $\delta(CDCl_3)$: 2.47(3H,s), 2.97(2H,t,J=6Hz), 3.83(3H,s), 3.90(3H,s), 4.27(2H,t,J=6Hz), 6.57(1H,d,J=8Hz), 7.2-8.1(5H).

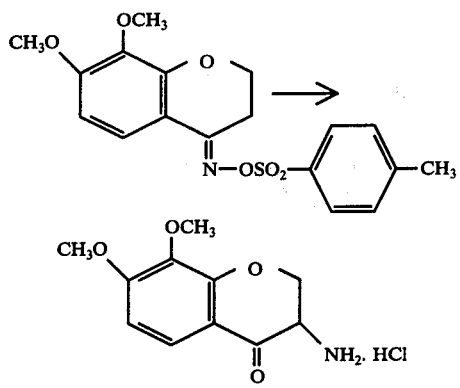

A solution prepared from 20 volume parts of dry ethanol and 1 part of potassium metal is cooled to 0° to −5° C and a solution of 7.5 parts of 7,8-dimethoxychromanone-(4) O-(p-toluenesulfonyl)-oxime in 25 volume parts of benzene is added dropwise. After the addition has been completed, the mixture is stirred at that temperature for 2 hours and, then, further stirred at room temperature overnight. The precipitate is filtered off and, under stirring, cold dilute hydrochloric acid is added dropwise to the filtrate. The addition of dilute hydrochloric acid is stopped when the reaction mixture has ceased to assume a red color, after which the mixture is stirred at 5° to 10° C for 1 hour. The water layer is separated from the organic layer and the former is washed three times with 50 volume parts portions of benzene. The water layer is concentrated and the residue is recrystallized from ethanol. The procedure gives colorless platelets of 7,8-dimethoxy-3-aminochromanone-(4) hydrochloride. Melting point: 204°-206° C.

Elemental analysis, $C_{11}H_{14}NO_4Cl_1 \cdot 1/3H_2O$: Calcd.: C, 49.72; H, 5.56; N, 5.27. Found: C, 49.76; H, 5.37; N, 5.20.

Infrared absorption spectrum, $\gamma KBr/max$ cm$^{-1}$: 3400, 2900-2400, 1690, 1600

Nuclear magnetic resonance spectrum($d_6$-DMSO), $\delta$: 3.72 (3H,s), 3.88(3H,s), 4.30-4.7(2H), 4.90(1H,d,J=5Hz), 6.88(1H,d,J=9Hz), 7.56(1H,d,J=9Hz), 9.0(2H)

REFERENCE EXAMPLE 2

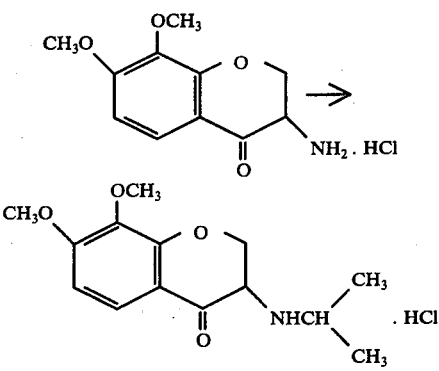

In a mixture of 8 volume parts of methanol and 20 volume parts of acetone is dissolved 0.26 part of 7,8-dimethoxy-3-aminochromanone-(4) hydrochloride. While the solution is stirred under cooling with ice, 0.20 part of the molecular compound (LiBH$_3$CN.2C$_4$H$_8$O$_2$) of 1 mole of lithium cyanoborohydride and 2 moles of dioxane is added dropwise over a period of about 1 hour. The mixture is further stirred under cooling with ice for 1 hour, after which time it is concentrated at a temperature not exceeding 20° C. The residue is extracted by the addition of 100 volume parts of ethyl acetate and the extract is washed with a saturated aqueous solution of sodium chloride. The ethyl acetate layer is dehydrated over anhydrous sodium sulfate and filtered.

To the filtrate is added ethyl saturated with hydrogen chloride and the resultant crystals are harvested by filtration. Recrystallization from ethanol-acetone gives colorless prisms of 7,8-dimethoxy-3-isopropylamino-chromanone-(4) hydrochloride. Melting point: 187°-189° C.

Elemental analysis, $C_{14}H_{19}NO_4 \cdot HCl$: Calcd.: C, 55.72; H, 6.68; N, 4.64. Found: C, 55.51; H, 6.68; N, 4.75.

Infrared absorption spectrum, $\gamma KBr/max$ cm$^{-1}$: 3400, 2900-2400, 1690, 1600

Nuclear magnetic resonance spectrum($d_6$-DMSO) $\delta$: 1.29, 1.32 (6H,dd,J=6Hz), 3.70(3H,s), 3.87(3H,s), 3.2-3.8(2H,m), 4.5-4.8(2H,m), 4.96(1H,d,J=6Hz), 6.85(1H,d,J=9Hz), 7.55(1H,d,J=9Hz)

REFERENCE EXAMPLE 3

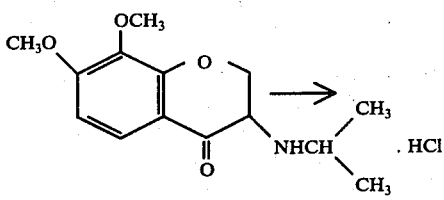

-continued

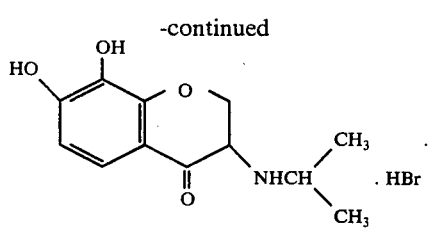

To 0.21 part of 7,8-dimethoxy-3-isopropylaminochromanone-(4) hydrochloride is added 2 volume parts of a 48% aqueous solution of hydrogen bromide and the mixture is heated on reflux for 1.5 hour. (During this operation, the oil bath temperature is maintained at or below 150° C). The reaction mixture is concentrated under reduced pressure and the concentrate is dissolved in 30 volume parts of ethanol. The solution is treated with activated carbon and, then, the ethanol is distilled off. The residue is crystallized by the addition of acetone and the crystals are harvested by filtration. Recrystallization from ethyl ether-ethanol gives colorless prisms of 7,8-dihydroxy-3-isopropylaminochromanone-(4) hydrobromide. Melting point: 226°–228° C(decomp.).

Elemental analysis, $C_{12}H_{15}NO_4 \cdot HBr$: Calcd.: C, 45.29; H, 5.07; N, 4.40. Found: C, 44.87; H, 5.85; N, 3.97.

Infrared absorption spectrum, $\gamma KBr/max$ $cm^{-1}$: 3520, 3300–3100, 2900–2450, 1690, 1620

Nuclear magnetic resonance spectrum($d_6$-DMSO) δ : 1.30, 1.34(6H,d,J=7Hz), 3.4–3.8(2H), 4.3–5.0(3H), 6.60(1H,d,J=8Hz), 7.20(1H,d,J=8Hz), 9.0–9.2(1H).

REFERENCE EXAMPLE 4

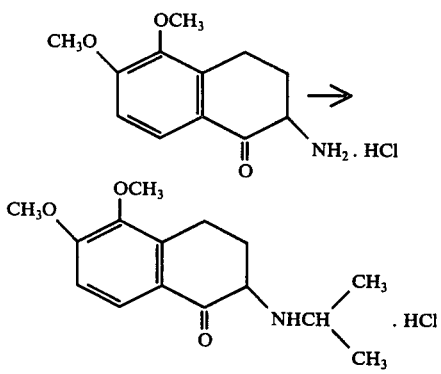

In a mixture of 3 volume parts of dry acetone and 5 volume parts of dry ethanol, there is dissolved 0.075 part of 3,4-dihydro-2-amino-5,6-dimethoxy-1(2H)-naphthalenone hydrochloride. While the solution is held at 0° C and with stirring, 0.080 part of the molecular compound of 1 mole of lithium cyanoborohydride and 2 moles of dioxane is added in small portions. After the addition has been completed, the mixture is stirred at 0° C for 3 hours and, then, 1N hydrochloric acid is added in sufficient amounts to bring the pH to 2 or less. The acetone and ethanol are distilled off under reduced pressure and the residue is neutralized by the addition of a 5% aqueous solution of sodium hydrogen carbonate, after which the basic matter is extracted with ethyl ether. The ethyl ether layer is washed with water and dehydrated over anhydrous sodium sulfate. Then, dry hydrogen chloride gas is bubbled into the solution. The ethyl ether is distilled off and the residue is recrystallized from a mixture of ethanol and ethyl ether. The procedure gives 3,4-dihydro-2-isopropylamino-5,6-dimethoxy-1(2H)-naphthalenone hydrochloride. Melting point: 141°–157° C (decomp).

Elemental analysis, $C_{15}H_{21}NO_3 \cdot HCl$: Calcd.: C, 60.09; H, 7.40; N, 4.67. Found: C, 59.70; H, 7.48; N, 4.62.

Infrared absorption spectrum, $\gamma KBr/max$ $cm^{-1}$ 3000–2400, 1695, 1600, 1500, 1285, 1075, 810

Nuclear magnetic resonance spectrum($D_2O$, external reference) δ : 1.47(6H), 3.85(3H), 7.13(1H), 7.85(1H)

REFERENCE EXAMPLE 5

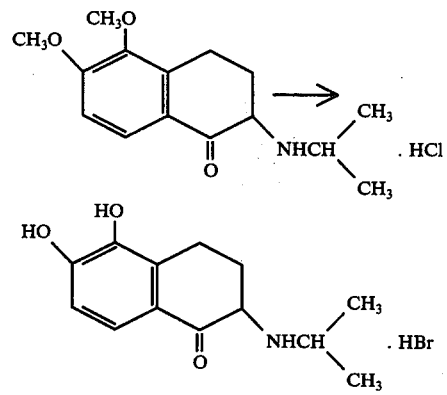

In a mixture of 2 volume parts of a 48% aqueous solution of hydrogen bromide and 0.75 volume part of acetic anhydride, there is dissolved 0.20 part of 3,4-dihydro-2-isopropylamino-5,6-dimethoxy-1-(2H)-naphthalenone hydrochloride and the solution is heated in a sealed tube at 140° to 150° C for 2 hours. The reaction mixture is treated with activated carbon and the filtrate is concentrated in the routine manner, whereupon crystals of 3,4-dihydro-2-isopropylamino-5,6-dihydro-1(2H)-naphthalenone hydrobromide are obtained. Melting point: 220° to 225° C(decomp.)

Elemental analysis, $C_{13}H_{17}NO_3 \cdot HBr$: Calcd.: C, 49.38; H, 5.74; N, 4.43. Found: C, 49.24; H, 5.67; N, 4.19.

Infrared absorption spectrum, $\gamma KBr/max$ $cm^{-1}$ : 3500–2400, 1680, 1610, 1300, 900, 820

Nuclear magnetic resonance spectrum($D_2O$, external reference) δ : 1.46–1.58(6H), 2.00–4.60(6H), 7.54(1H )

REFERENCE EXAMPLE 6

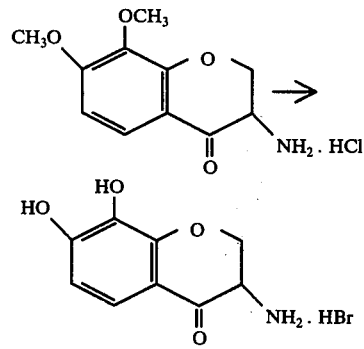

In 10 volume parts of a 48% aqueous solution of hydrogen bromide (b.p.126° to 127° C), 1.8 parts of 7,8-dimethoxy-3-aminochromanone-(4) hydrochloride is heated on reflux for 2 hours. The reaction mixture is then cooled, whereupon crystals separate. The crystals are harvested by filtration and recrystallized from a mixture of ethanol and water. The procedure gives colorless needles of 7,8-dihydroxy-3-aminochromanone-(4) hydrobromide. Melting point: 255° C.

Elemental analysis, $C_9H_{10}BrNO_4 \cdot H_2O$: Calcd.: C, 36.75; H, 4.11; N, 4.76. Found: C, 36.75; H, 4.02; N, 4.59.

Infrared absorption spectrum γKBr/max cm$^{-1}$: 3330–3000, 1680, 1620, 1595

Nuclear magnetic resonance spectrum($d_6$-DMSO) δ : 4.2–4.6 (2H,m), 4.75(1H,d,J=7.3Hz), 6.56(1H,d,J=9Hz), 7.16(1H,d,J=9Hz), 8.3–8.7(3H).

REFERENCE EXAMPLE 7

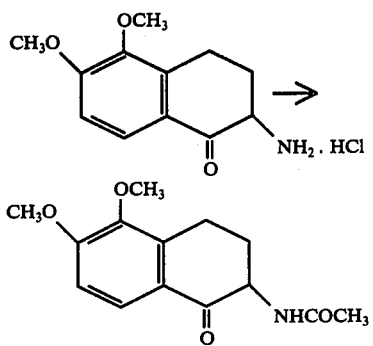

In a mixture of 10 volume parts of pyridine and 10 volume parts of acetic anhydride, there is dissolved 2.0 parts of 3,4-dihydro-2-amino-5,6-dimethoxy-1(2H)-naphthalenone hydrochloride and the solution is stirred at room temperature for 15 hours. It is then poured in about 50 parts of icewater, followed by the addition of 3N hydrochloric acid to bring the solution to sufficient acidity. The solution is extracted with chloroform. The chloroform layer is washed with 3 N hydrochloric acid and water and, after drying over anhydrous sodium sulfate, the chloroform is distilled off. The residue is recrystallized from ethanol, whereupon 3,4-dihydro-2-acetamido-5,6-dimethoxy-1(2H)-naphthalenone is obtained as colorless crystals. Melting point: 155°–158° C.

Elemental analysis, $C_{14}H_{17}NO_4$ Calcd.: C, 63.86; H, 6.51; N, 5.32. Found C, 63.68; H, 6.37; N, 5.18.

Infrared absorption spectrum(in CHCl$_3$): 3400, 3000, 1660, 1590, 1490, 1280, 1080

Nuclear magnetic resonance spectrum(CDCl$_3$) δ : 2.2(3H), 2.8–3.6(4H), 3.85(3H), 3.97(3H), 4.30–4.90(1H), 6.47–6.98(1H), 6.98(1H), 7.90(1H)

REFERENCE EXAMPLE 8

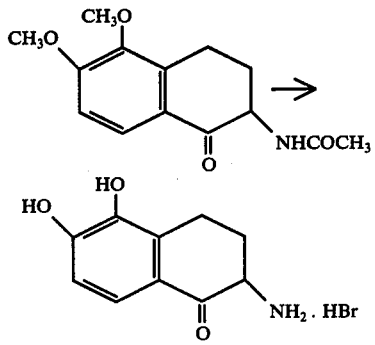

In 2 volume parts of a 48% aqueous solution of hydrogen bromide is dissolved 0.10 part of 3,4-dihydro-2-acetamido-5,6-dimethoxy-1-(2H)-naphthalenone and the solution is heated in a sealed tube at 150° C for 4 hours. The reaction mixture is treated with activated carbon and the filtrate is concentrated, whereupon 3,4-dihydro-2-amino-5,6-dihydroxy-1 (2H)-naphthalenone hydrobromide is obtained as colorless crystals. This product shows no definite melting point (250° to 290° C) (decomp.).

Infrared absorption spectrum, γKBr/max cm$^{-1}$: 3500–2800, 1660, 1605, 1580, 1490, 1380, 1310, 1280, 1025, 905, 820

Nuclear magnetic resonance spectrum($D_2O$, external reference) δ : 2.00–3.30(4H), 4.18–4.40(1H), 6.80(1H), 7.40(1H)

REFERENCE EXAMPLE 9

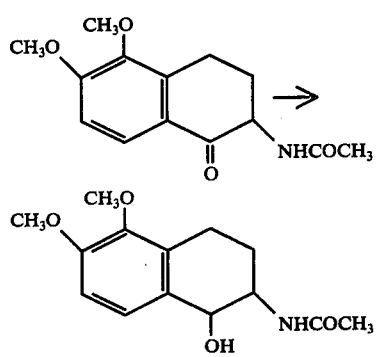

To a suspension of 0.32 part of lithium aluminum hydride in dry tetrahydrofuran, there is added 1.6 parts of 3,4-dihydro-2-acetamido-5,6-dimethoxy-1-(2H-naphthalenone in small portions. After the addition has been completed, the mixture is further stirred for 20 minutes, at the end of which time water is added so as to decompose the lithium aluminum hydride. The mixture is rendered sufficiently alkaline by the addition of a 3N aqueous solution of sodium hydroxide and, then, extracted with chloroform. The chloroform layer is washed with water and dried over anhydrous sodium sulfate. The chloroform is distilled off and the residue is treated with ethanol. The procedure gives crystals of 1-hydroxy-2-acetamido-5,6-dimethoxy-1,2,3,4-tetrahydronaphthalene. Melting point 184°–186° C.

Elemental analysis, $C_{14}H_{19}NO_4$ Calcd. C, 63.38; H, 7.22; N, 5.28 Found: C, 63.00; H, 7.14; N, 5.33

Nuclear magnetic resonance spectrum(CDCl$_3$ + $d_6$-DMSO) δ : 2.00, 3.80, 3.87, 6.80–7.40, 6.83, 7.27

Nuclear magnetic resonance spectrum(CDCl$_3$ + $d_6$DMSO + $D_2O$) δ : 4.43

Infrared absorption spectrum, δKBr/max cm$^{-1}$: 3300–2700, 1650, 1570, 1495, 1280, 1090, 1070, 1030, 1015

EXAMPLE 1

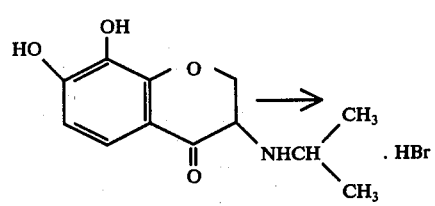

-continued

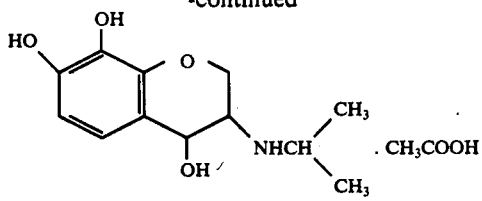

To 0.20 part of 7,8-dihydroxy-3-isopropylamino-chromanone-(4) hydrobromide are added 25 volume parts of water and 0.10 part of palladium black, and catalytic reduction is carried out in a current of hydrogen gas. In about 3 hours, 20 volume parts of hydrogen is absorbed (15 volume parts, theoretically). The catalyst is filtered off and the filtrate is promptly freeze-dried. The residue is dissolved in 30 volume parts of methanol and, then, 0.082 part of anhydrous sodium acetate is added and dissolved. The solution is concentrated at a temperature not exceeding 20° C and with the addition of 50 volume parts of dry tetrahydrofuran, the concentrate is stirred well. The insoluble matter (sodium bromide) is filtered off and the filtrate is concentrated at a temperature not exceeding 20° C. The residue is dissolved in 20 volume parts of tetrahydrofuran, followed by the addition of 20 volume parts of ethyl acetate. The mixture is concentrated, whereupon cis-7,8-dihydroxy-3-isopropylaminochromanol-(4) acetate is obtained as white powders. Melting point: 83°-84° C.

Elemental analysis, $C_{12}H_{17}NO_4 \cdot CH_3COOH \cdot H_2O$: Calcd.: C, 52.99; H, 7.31; N, 4.41. Found: C, 52.98; H, 6.89; N, 4.22.

Infrared absorption spectrum, γKBr/max cm$^{-1}$: 3400(OH), 3200-2400(OH,

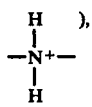

1570(COO$^-$)

Nuclear magnetic resonance spectrum(d$_6$-DMSO) δ : 1.04, 1.06(6H,d,J=8Hz), 2.8-3.2(2H,m), 1.91(3H,s), 3.6-4.1 (3H,m) 4.45(1H,d,J=3Hz), 6.32(1H,d,J=8Hz), 6.53 (1H,d,J=8Hz)

EXAMPLE 2

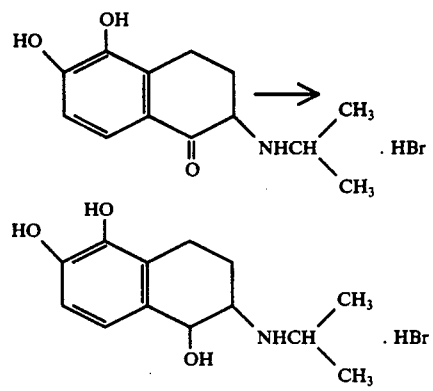

In 10 volume parts of water is dissolved 0.180 part of 3,4-dihydro-2-isopropylamino-5,6-dihydroxy-1(2H)-naphthalenone hydrobromide and with the addition of 0.2 part of 5 % palladium-on-carbon, catalytic reduction is carried out in a current of hydrogen gas. The absorption of hydrogen ceases when 9 volume parts of hydrogen has been absorbed. The catalyst is filtered off and the filtrate is freeze-dried. Finally, the residue is recrystallized from ethanol-ethyl ether. The procedure gives colorless prisms of 1,5,6-trihydroxy-2-isopropylamino-1,2,3,4-tetrahydronaphthalene hydrobromide. Melting point: 169° C(decomp.)

Infrared absorption spectrum, γKBr/max cm$^{-1}$: 3350, 3140, 2900-2400, 1620, 1595

Nuclear magnetic resonance spectrum(d$_6$-DMSO) δ : 1.28, 1.33 (6H,d,J=6Hz), 4.64(1H,t,J=7Hz)

EXAMPLE 3

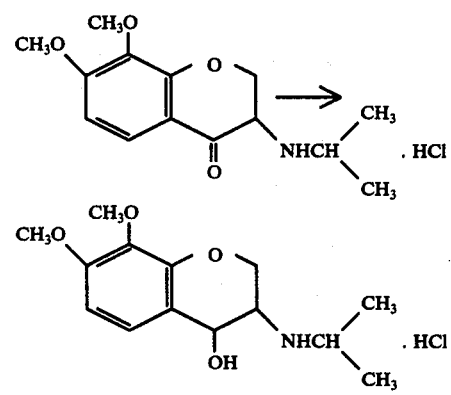

In 10 volume parts of distilled water is dissolved 0.20 part of 7,8-dimethoxy-3-isopropylaminochromanone-(4) hydrochloride and the solution is shaken in hydrogen streams together with 0.30 part of 5 % palladium-on-carbon. In about 40 minutes, 18 volume parts of hydrogen is absorbed. The reaction mixture is filtered and the filtrate is freeze-dried. The residue is dissolved in ethanol, followed by the addition of ethyl ether. Thus, in a little turbid condition, the solution is left standing in the cold for a week, whereupon cis-7,8-dimethoxy-3-isopropylaminochromanol-(4) hydrochloride separates as colorless prisms. Melting point: 182° C.

Infrared absorption spectrum, γKBr/max cm$^{-1}$: 2900-2300, 1605

Nuclear magnetic resonance spectrum(d$_6$-DMSO) δ :1.36(6H,d,J=6Hz), 3.67(3H,s), 3.77(3H,s), 3.4–4.6(4H,m), 4.84 (1H,d,J=3Hz), 6.68(1H,d,J=8Hz), 7.06(1H,d,J=8Hz)

EXAMPLE 4

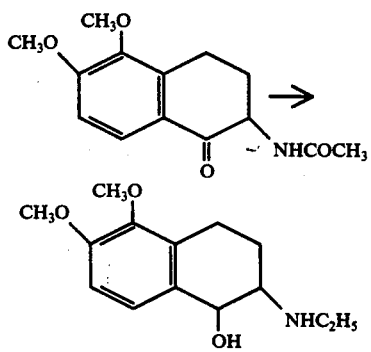

To a mixture of 0.733 part of 3,4-dihydro-2-acetamido-5,6-dimethoxy-1(2H)-naphthalenone and 0.132 part of lithium aluminum hydride, there is added 15 volume parts of dry tetrahydrofuran and the mixture is refluxed for 3.5 hours.

The mixture is rendered sufficiently acid by the addition of 3N hydrochloric acid and, then, extracted with chloroform to remove the non-basic matter. Then, the water layer is rendered alkaline with a 2N aqueous solution of sodium hydroxide and the basic matter is extracted with ethyl ether. The ethyl ether is distilled off and the residue is recrystallized from isopropyl ether. The procedure gives crystals of 1-hydroxy-2-ethylamino-5,6-dimethoxy-1,2,3,4-tetrahydronaphthalene. Melting point: 125°–128° C.

Elemental analysis, $C_{14}H_{21}NO_3$: Calcd. C, 66.90; H, 8.42; N, 5.57. Found: C, 66.62; H, 8.50; N, 5.41.

Nuclear magnetic resonance spectrum (CDCl$_3$) δ : 1.17(3H), 2.00–3.20(8H), 3.82(3H), 3.87(3H), 4.40(1H), 6.82(1H), 7.27(1H)

Infrared absorption spectrum. γKBr/max cm$^{-1}$: 3400–2800, 1610, 1490, 1280, 1090, 1010, 770, 760, 705

EXAMPLE 5

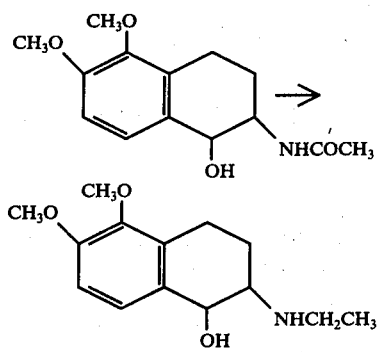

In 2 volume parts of dry tetrahydrofuran is suspended 0.016 part of lithium aluminum hydride, followed by the addition of 0.053 part of 1-hydroxy-2-acetamido-5,6-dimethoxy-1,2,3,4-tetrahydronaphthalene in small portions. The mixture is refluxed for 4 hours.

After cooling, the reaction mixture is rendered sufficiently acid with 3N hydrochloric acid, and ethyl ether is added, followed by stirring. The water layer is made alkaline with a 2N aqueous solution of sodium hydroxide and, then, the basic matter is extracted with ethyl ether. The ethyl ether layer is dried in the routine manner and the ethyl ether is distilled off. Finally the residue is recrystallized from isopropyl ether to obtain 1-hydroxy-2-ethylamino-5,6-dimethoxy-1,2,3,4-tetrahydronaphthalene.

The infrared absorption and nuclear magnetic resonance spectra of this compound are in agreement with the corresponding spectra of the 1-hydroxy-2-ethylamino-5,6-dimethoxy-1,2,3,4-tetrahydronaphthalene sample prepared by the procedure set forth in Example 4.

EXAMPLE 6

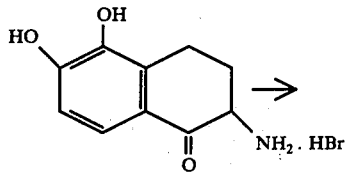

-continued

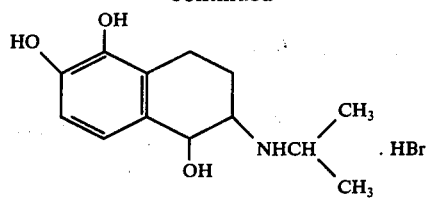

In a mixture of 1 volume part of acetone and 10 volume parts of ethanol, there is dissolved 0.100 part of 3,4-dihydro-2-amino-5,6-dihydroxy-1(2H)-naphthlenone hydrobromide and with the addition of 0.0115 part of platinum dioxide and 0.038 part of anhydrous sodium acetate, catalytic reduction is carried out in a current of hydrogen gas. After a substantially stoichiometric amount of hydrogen gas has been absorbed, 0.4 volume part of a 48 % aqueous solution of hydrogen bromide is added. The mixture is filtered and the filtrate is concentrated. A small amount of ethanol is added to the residue and, after the insolubles are removed, the filtrate is concentrated a second time. Finally the residue is recrystallized from acetone. The procedure gives 1,5,6-trihydroxy-2-isopropylamino-1,2,3,4-tetrahydronaphthalene hydrobromide. Melting point: 167° to 169° C(decomp.)

EXAMPLE 7

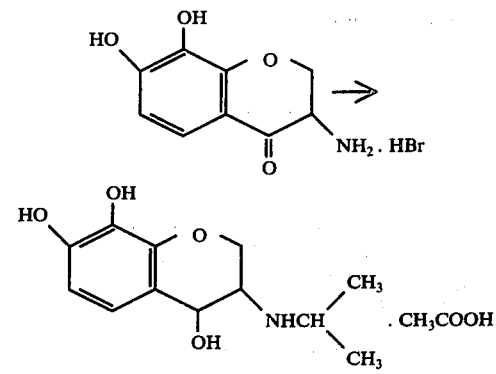

In 40 volume parts of methanol is dissolved 0.800 part of 7,8-dihydroxy-3-aminochromanone-(4) hydrobromide, and using 1 part of 5 % palladium-on-carbon as a catalyst, catalytic reduction is carried out in a current of hydrogen gas until a substantially stoichiometric amount of hydrogen is absorbed. The reaction mixture is filtered and 1 volume part of acetone and 0.450 part of sodium acetate are added to the filtrate.

Then, reductive alkylation is carried out using platinum dioxide as a hydrogenation catalyst. The reaction mixture is filtered and the filtrate is concentrated under reduced pressure. The residue is dissolved in 50 volume parts of dry tetrahydrofuran and, after the insoluble matter has been filtered off, the filtrate is concentrated. The procedure gives white powders of cis-7,8-dihydroxy-3-isopropylaminochromanol-(4) acetate.

EXAMPLE 8

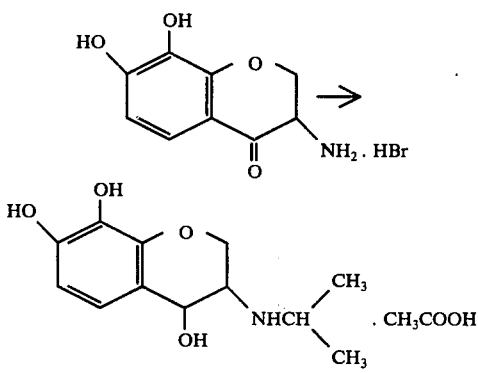

In a current of hydrogen gas, 0.800 part of 7,8-dihydroxy-3-aminochromanone-(4) hydrobromide is catalytically reduced for about 24 hours, using 40 volume parts of methanol, 0.450 part of sodium acetate and 1 part of 5 % palladium-on-carbon. The reaction mixture is filtered to remove the palladium-on-carbon, and with platinum dioxide and 1 volume part of acetone, the methanolic solution is further subjected to reductive alkylation in hydrogen streams. In about 5 hours, 59 volume parts of hydrogen is absorbed. The catalyst is filtered off and the filtrate is concentrated under reduced pressure. To the residue is added 80 volume parts of dry tetrahydrofuran and, after stirring well, the inorganic matter is filtered off. The filtrate is concentrated and the concentrate is recrystallized from tetrahydrofuran-ethyl acetate. The procedure gives white powders of trans-7,8-dihydroxy-3-isopropylaminochromanol-(4) acetate. Melting point: 115°–117° C.

Infrared absorption spectrum, $\gamma$KBr/max cm$^{-1}$: 3400–3200

Nuclear magnetic resonance spectrum($d_6$-DMSO) $\delta$ : 0.99(6H,d,J=6Hz), 1,88(3H,s), 2.7–3.1(2H,m), 3.7–4.15(2H,m), 4.18(1H,d,J=6Hz), 6.0–6.4(4H,broad), 6.29(1H,d,J=8Hz), 6.55(1H,d,J=8Hz)

Elemental analysis, $C_{12}H_{17}NO_4 \cdot CH_3COOH$: Calcd.: C, 56.17; H, 7.07; N, 4.68. Found: C, 56.10; H, 7.17; N, 4.37.

EXAMPLE 9

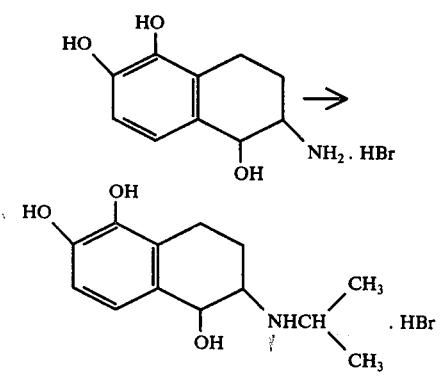

In a mixture of 10 volume parts of dry ethanol and 10 volume parts of dry acetone, there is dissolved 0.500 part of 1,5,6-trihydroxy-2-amino-1,2,3,4-tetrahydronaphthalene hydrobromide and, with the addition of 2 volume parts of triethylamine, the solution is stirred in nitrogen streams at room temperature for 2 hours. To the reaction mixture is added 1.5 volume parts of 1N hydrobromic acid and the solvent is removed under reduced pressure.

The residue is dissolved in 10 volume parts of ethanol and, with the addition of 0.500 part of 5 % palladium-in-carbon, catalytic reduction is carried out in a current of hydrogen gas until a substantially stoichiometric amount of hydrogen gas is absorbed. The reaction mixture is filtered and the filtrate is concentrated at low temperature. Finally, the concentrate is recrystallized from a mixture of alcohol and ethyl ether. The procedure gives 1,5,6-trihydroxy-2-isopropylamino-1,2,3,4-tetrahydronaphthalene hydrobromide. Melting point: 168° C(decomp.).

EXAMPLE 10

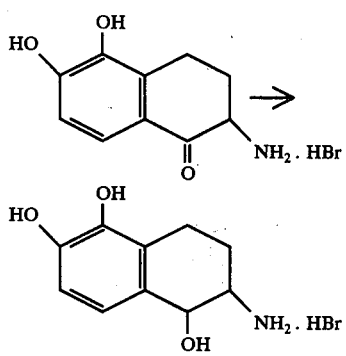

In 5 volume parts of water is dissolved 0.200 part of 3,4-dihydro-2-amino-5,6-dihydroxy-1(2H)-naphthalenone hydrobromide and, using 0.050 part of platinum dioxide, the catalytic reduction is carried out in a current of hydrogen gas until a substantially stoichiometric amount of hydrogen gas is absorbed. The catalyst in the reaction mixture is filtered off and to the filtrate is added a mixture of ethyl ether, methanol and water. The procedure gives white prisms of 2-amino-1,5,6-trihydroxy-1,2,3,4-tetrahydronaphthalene hydrobromide. Melting point: 190° to 200° C(decomp.)

Elemental analysis $C_{10}H_{13}O_3N \cdot HBr \cdot H_2O$: Calcd.: C, 40.84; H, 5.48; N, 4.76. Found: C, 40.49; H, 5.37; N, 4.61.

Nuclear magnetic resonance spectrum, ($d_6$-DMSO) $\delta$ 1.8(4H), 3.16–3.40(2H), 4.30(1H), 5.4–5.6(1H), 6.4–7.4(5H), 7.6–8.3(2H)

EXAMPLE 11

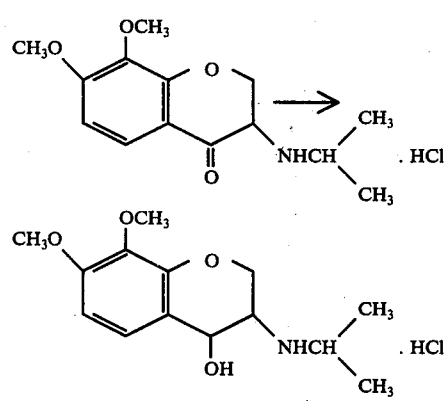

In 10 volume parts of water is dissolved 0.200 part of 7,8-dimethoxy-3-isopropylaminochromanone-(4) hydrochloride and with the addition of 0.300 part of palladium black, catalytic reduction is carried out in a current of hydrogen gas. The absorption of hydrogen ceases when a substantially stoichiometric amount of hydrogen gas has been absorbed. The catalyst is filtered off and the filtrate is freeze-dried. Finally, the residue is recrystallized from ethanolethyl ether. The procedure gives colorless prisms of 7,8-dimethoxy-3-isopropylaminochromanol-(4) hydrochloride. Melting point: 182° C.

Elemental analysis, $C_{14}H_{22}ClNO_4 \cdot 1/4H_2O$: Calcd.: C, 54.5;H, 7.37; N, 4.54. Found: C, 54.7; H, 7.37; N, 4.56.

Infrared absorption spectrum $\gamma KBr/max$ $cm^{-1}$: 2900–2300, 1605

Nuclear magnetic resonance spectrum($d_6$-DMSO) $\delta$ : 1.36(6H,d,J=6Hz), 3.67(3H,s), 3.77(3H,s), 3.4–4.6 (4H,m), 4.84(1H,d,J=3Hz), 6.68(1H,d,J=8Hz), 7.06 (1H,d,J=8Hz)

EXAMPLE 12

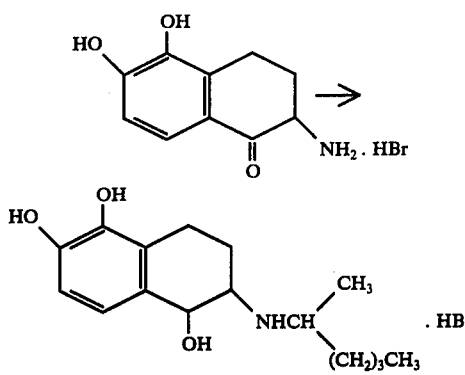

In a mixture of 10 volume parts of methanol and 2 volume parts of methyl-n-butylketone is dissolved 0.100 part of 3,4-dihydro-2-amino-5,6-dihydroxy-1(2H)-naphthalenone hydrobromide, and with the addition of 0.0115 part of platinum dioxide and anhydrous sodium acetate, the catalytic reduction is carried out in a current of hydrogen gas. After a substantially stoichiometric amount of hydrogen gas has ben absorbed, a small amount of 48% aqueous solution of hydrogen bromide is added. The mixture is filtered and filtrate is concentrated. A small amount of ethanol is added to the concentrate and, after the insolubles are removed, the filtrate is concentrated. The procedure gives 1,5,6-trihydroxy-2-(2-hexyl)-amino-1,2,3,4-tetrahydronaphthalene hydrobromide.

Nuclear magnetic resonance spectrum ($D_2O$) $\delta$ : 0.64–2.00 (12H), 2.86–3.16(4H), 3.80–4.48(1H), 6.46–7.04(2H)

EXAMPLE 13

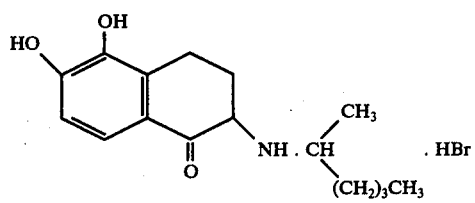

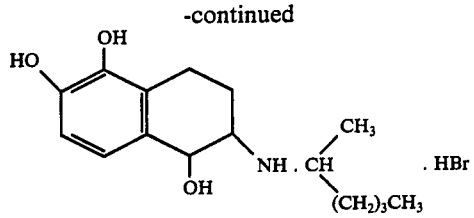

In 10 volume parts of water is dissolved 0.200 part of 3,4-dihydro-2-(2-hexyl)-amino-5,6-dihydroxy-1(2H)-naphthalenone hydrobromide and, with the addition of 0.200 part of a palladium black, catalytic reduction is carried out until a substantially stoichiometric amount of hydrogen gas is absorbed. The catalyst is filtered off and the filtrate is freeze-dried. The residue is dissolved in ethanol, followed by the addition of ethyl ether. The procedure gives 1,5,6-tri-hydroxy-2-(2-hexyl)-amino-1,2,3,4-tetrahydronaphthalene. The nuclear magnetic resonance spectra of this compound are in agreement with those of the compound prepared in Example 12.

EXAMPLE 14

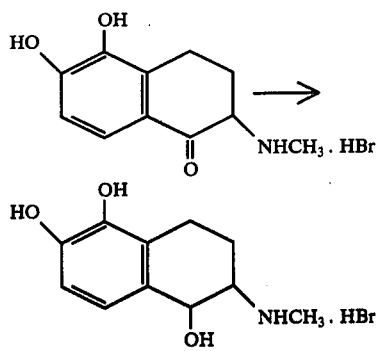

In 5 volume parts of water is dissolved 0.200 part of 3,4-dihydro-2-methylamino-5,6-dihydroxy-1(2H)-naphthalenone hydrobromide and, using 0.050 part of platinum dioxide, the catalytic reduction is carried out in a current of hydrogen gas until a substantially stoichiometric amount of hydrogen gas is absorbed. The catalyst in the reaction mixture is filtered off and to the filtrate is added a mixture of ethyl ether, methanol and water. The procedure gives white prisms of 2-methylamino-1,5,6-trihydroxy-1,2,3,4-tetrahydronaphthalene hydrobromide. Melting point: 165° to 169° C(decomp.)

Elemental analysis, $C_{11}H_{15}O_3N \cdot HB_r \cdot 1/2H_2O$: Calcd.: C, 44.16; H, 5.73; N, 4.68. Found: C, 44.11; H, 5.40; N, 4.45.

Nuclear magnetic resonance spectrum, ($d_6$-DMSO) $\delta$ : 2.7(3H), 4.6(1H), 6.6–6.8(2H)

What we claim is:

1. A compound selected from the group consisting of compounds of the formula

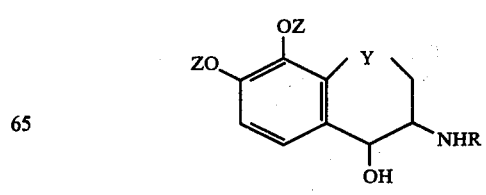

wherein Y represent methylene, Z represents hydrogen and R represents hydrogen or alkyl of 1 to 6 carbon atoms, and pharmaceutically acceptable salts thereof.

2. A compound as claimed in claim 1, wherein R is hydrogen.

3. A compound as claimed in claim 1, wherein R is alkyl of 1 to 6 carbon atoms.

4. The compound as claimed in claim 1, namely 2-methylamino-1,5,6-trihydroxy-1,2,3,4-tetrahydronaphthalene.

5. The compound as claimed in claim 1, namely 2-amino-1,5,6-trihydroxy-1,2,3,4-tetrahydronaphthalene.

6. The compound as claimed in claim 1, namely 1,5,6-trihydroxy-2-isopropylamino-1,2,3,4-tetrahydronaphthalene.

7. The compound as claimed in claim 1, namely 1,5,6-trihydoxy-2-(1,3-dimethylbutyl)-amino-1,2,3,4-tetrahydronaphthalene.

8. The compound as claimed in claim 1, namely 1,5,6-trihydroxy-2-(2-hexyl)-amino-1,2,3,4-tetrahydronaphthalene.

* * * * *